(12) United States Patent
Swayze et al.

(10) Patent No.: US 10,568,701 B2
(45) Date of Patent: Feb. 25, 2020

(54) ROBOTIC SURGICAL SYSTEM WITH VIRTUAL CONTROL PANEL FOR TOOL ACTUATION

(71) Applicant: Ethicon LLC, Guaynabo, PR (US)

(72) Inventors: Jeffrey S. Swayze, West Chester, OH (US); Joshua Young, Loveland, OH (US); Andrew Beckman, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 259 days.

(21) Appl. No.: 15/383,026

(22) Filed: Dec. 19, 2016

(65) Prior Publication Data

US 2018/0168733 A1 Jun. 21, 2018

(51) Int. Cl.
*A61B 34/20* (2016.01)
*A61B 34/00* (2016.01)
(Continued)

(52) U.S. Cl.
CPC .............. *A61B 34/20* (2016.02); *A61B 1/313* (2013.01); *A61B 5/0036* (2018.08);
(Continued)

(58) Field of Classification Search
CPC ....... A61B 34/20; A61B 5/0036; A61B 5/064; A61B 5/0084; A61B 1/313; A61B 5/743; A61B 90/37; A61B 34/25; A61B 90/361; A61B 34/30; A61B 1/06; A61B 1/04; A61B 2034/256; A61B 2090/365;
(Continued)

(56) References Cited

U.S. PATENT DOCUMENTS 7,996,110 B2 * 8/2011 Lipow .................... G09B 23/28
318/568.11
8,114,345 B2 2/2012 Dlugos, Jr. et al.
(Continued)

FOREIGN PATENT DOCUMENTS

| WO | WO-2014151621 A1 | 9/2014 |
| WO | WO-2016133644 A1 | 8/2016 |
| WO | WO-2016149345 A1 | 9/2016 |

OTHER PUBLICATIONS

International Search Report and Written Opinion for International App. No. PCT/US2017/064586 dated Mar. 23, 2018 (15 pages).

*Primary Examiner* — Jason Holloway
(74) *Attorney, Agent, or Firm* — Mintz Levin Cohn Ferris Glovsky and Popeo, P.C.

(57) ABSTRACT

A surgical system includes a detector, comprising an array of pixels configured to detect light reflected by a surgical instrument and generate a first signal comprising a first dataset representative of a visible image of the surgical instrument. The surgical system also includes a processor configured to receive the first signal, generate a modified image of the surgical instrument that includes a control panel. The control panel includes one or more control elements representative of one or more operating parameters of the surgical instrument. The processor is further configured to receive an input to the control panel from a user, the input being effective to change one of the operating parameters. The processor is also configured to generate a command signal based on the input to change the one of the operating parameters.

14 Claims, 7 Drawing Sheets

(51) Int. Cl.
    *A61B 34/30*     (2016.01)
    *A61B 90/00*     (2016.01)
    *A61B 5/00*     (2006.01)
    *G06K 9/20*     (2006.01)
    *A61B 5/06*     (2006.01)
    *A61B 1/313*     (2006.01)
    *A61B 1/06*     (2006.01)
    *A61B 34/37*     (2016.01)
    *A61B 1/04*     (2006.01)
    *A61B 17/29*     (2006.01)

(52) U.S. Cl.
    CPC ............ *A61B 5/0084* (2013.01); *A61B 5/064* (2013.01); *A61B 5/743* (2013.01); *A61B 34/25* (2016.02); *A61B 34/30* (2016.02); *A61B 90/361* (2016.02); *G06K 9/209* (2013.01); *A61B 1/04* (2013.01); *A61B 1/06* (2013.01); *A61B 17/29* (2013.01); *A61B 34/37* (2016.02); *A61B 2034/2065* (2016.02); *A61B 2034/2068* (2016.02); *A61B 2034/256* (2016.02); *A61B 2090/373* (2016.02); *A61B 2090/3937* (2016.02); *G06K 2209/057* (2013.01)

(58) Field of Classification Search
    CPC ...... A61B 2034/2065; A61B 2090/373; A61B 34/37; A61B 17/29; A61B 2034/2068; G06K 2209/057; G06K 9/00671
    See application file for complete search history.

(56) References Cited

U.S. PATENT DOCUMENTS

| | | | |
|---|---|---|---|
| 10,398,517 B2 * | 9/2019 | Eckert | A61B 34/30 |
| 2009/0036902 A1 * | 2/2009 | DiMaio | A61B 34/10 606/130 |
| 2009/0245600 A1 | 10/2009 | Hoffman et al. | |
| 2011/0306986 A1 * | 12/2011 | Lee | B25J 9/1689 606/130 |
| 2013/0038707 A1 | 2/2013 | Cunningham et al. | |
| 2014/0055489 A1 * | 2/2014 | Itkowitz | G06T 11/40 345/633 |
| 2015/0100066 A1 * | 4/2015 | Kostrzewski | A61B 34/30 606/130 |
| 2016/0081754 A1 * | 3/2016 | Kostrzewski | A61B 34/30 606/130 |
| 2018/0032130 A1 * | 2/2018 | Meglan | G02B 27/017 |
| 2018/0092706 A1 * | 4/2018 | Anderson | A61B 34/30 |
| 2018/0200002 A1 * | 7/2018 | Kostrzewski | G02C 7/049 |
| 2019/0076199 A1 * | 3/2019 | Kline | A61B 34/20 |

* cited by examiner

ROBOTIC SURGICAL SYSTEM WITH VIRTUAL CONTROL PANEL FOR TOOL ACTUATION

FIELD

Methods and devices are provided for minimally invasive surgery, and in particular for providing virtual control panel of a surgical instrument.

BACKGROUND

Minimally invasive surgical (MIS) instruments are often preferred over traditional open surgical instruments due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical environment with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical environment on a visual display at a location remote from the patient. The surgeon can typically perform the surgical procedure at the location remote from the patient whilst viewing the end effector movement on the visual display during the surgical procedure. While viewing typically a three-dimensional image of the surgical environment on the visual display, the surgeon performs the surgical procedures on the patient by manipulating master control devices at the remote location, which master control devices control motion of the remotely controlled instruments.

While significant advances have been made in the field of minimally invasive surgery, there remains a need for improved methods, systems, and devices for providing virtual control panel of a surgical instrument.

SUMMARY

Methods, devices, and systems are provided for displaying a modified image of a surgical environment wherein the modified image includes at least a portion of a surgical instrument and a control panel associated with the surgical instrument. The control panel displayed in the modified image is active in that functions associated with the surgical instrument can be actuated by interacting with various specific elements of the control panel displayed in the modified image.

A surgical system includes a detector comprising an array of pixels configured to detect light reflected by a surgical instrument and generate a first signal comprising a first dataset representative of a visible image of the surgical instrument. The surgical system also includes a processor configured to receive the first signal, generate a modified image of the surgical instrument that includes a control panel that includes one or more control elements representative of one or more operating parameters of at least one of the surgical system and the surgical instrument. The processor is further configured to receive an input to the control panel from a user, the input being effective to change one of the operating parameters. The processor is also configured to generate a command signal based on the input to the control panel to change one of the operating parameters.

The surgical system can vary in a number of ways. In one embodiment, the modified image is displayed on a display device. In another embodiment, the processor identifies from the first dataset data representative of the surgical instrument based on position of the detector with respect to the surgical instrument.

In one embodiment, at least one of the position and shape of the control panel in the modified image is adjusted based on the orientation of the surgical instrument. In another embodiment at least one of the position and shape of the control panel with respect to the surgical instrument remains fixed.

The surgical system includes an input device to receive the input from the user, and in one embodiment the input device is a user interface. In one embodiment, the processor generates a pointer that moves relative to the modified image based on the input by the user. In one embodiment the command signal is generated when the user actuates one of the one or more control elements using the user interface device.

The processor is also configured to receive a second signal representative of information related to the surgical instrument. The control panel is generated based on the second signal and data related to the surgical instrument that is stored in a database.

The surgical instrument can be any type of instrument that is used in a surgical procedure. In one embodiment the surgical instrument is one that includes functionalities including at least one of tissue cutting, tissue stapling, and delivery of energy to tissue.

In another aspect, a robotic surgical system includes a robotic arm, and a tool assembly removably coupled to the robotic arm and including a shaft extending distally from a housing and an end effector coupled to a distal end of the shaft, the end effector being configured to treat tissue. The robotic surgical system also includes a camera system configured to capture light reflected by at least one of the end effector and the shaft and generate a signal representative of a visible image of the at least one of the end effector and shaft. The robotic surgical system further includes a processor configured to receive the signal and generate a modified image of the at least one of the end effector and shaft that includes a control panel. The control panel in the modified image comprises one or more control elements representative of one or more operating parameters of the robotic surgical system. The processor is configured to receive an input to the control panel from a user, the input being effective to change one of the operating parameters, and generate a command signal based on the input to change the one of the operating parameters.

In one embodiment, the robotic surgical system includes a display device, which can be wall or table mounted or on an accessory (e.g., head set, glasses, etc.), configured to display a modified image of the end effector and the shaft. The robotic surgery system also includes an input device to receive the input from the user. In one embodiment the input device is a user input device. In another embodiment, the processor generates a pointer that moves relative to the modified image based on the input by the user.

In another aspect a surgical method includes receiving a first signal representative of an image of a surgical instrument and generating a modified image of the surgical instrument that includes a control panel. The control panel comprises one or more control elements representative of one or more operating parameters of at least one of the surgical system and the surgical instrument. The surgical method also includes receiving an input to the control panel from a user, the input being effective to change one of the operating parameters. The surgical method further includes generating a command signal based on the input to change the one of the operating parameters.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The systems, devices, and methods disclosed herein can be implemented using a robotic surgical system. WIPO Patent Publication No. WO 2014/151621 filed on Mar. 13, 2014 and entitled "Hyperdexterous Surgical System" is incorporated by reference.

In general, a surgical system is described that allows a user (e.g., a surgeon) to control the operation of surgical instruments. In particular, the surgical instruments controlled by the described system are advanced surgical tools, for example, endocutters, and/or tools that have functionalities including at least one of cutting tissue, stapling tissue, and delivering energy to tissue. The controls of advanced tools may not be easily mapped to those of standard robotic tools (e.g., graspers, needle drivers etc.). Therefore, there is a need to develop control systems that allow a user to seamlessly control advanced surgical tools during surgery. The systems and methods described herein, however, are not limited to advanced surgical tools, and can be applied to virtually any surgical instrument used in a surgical procedure, including robotic tools.

During a minimally invasive procedure, or any surgical procedure in which the surgical instrument is outside of the surgeon's natural field of view, an image of the surgical environment as well as relevant portions of the surgical instrument is typically generated and displayed on a display to the surgeon, such as on a video monitor. Such an image is typically displayed in real-time. In aspects of the system described herein, the image of the surgical instrument is modified to include a virtual control panel. The surgeon (or any other user) can interact with the control panel through a user interface device (e.g., one that is able to move in 3D space). The control panel can be pinned to a fixed location in the display, or can be moved to various locations in the modified image. For example, the location of the control panel can be fixed relative to a portion of the surgical instrument (e.g., shaft of a surgical instrument), and the control panel can follow the surgical instrument as it moves in the modified image. The control panel can change in size, shape, aspect ratio, and perspective to match the 2D or 3D orientation of the surgical instrument and/or the surrounding environment. Moreover, the control panel can appear in two dimensions (if viewed on a 2D display) or in three dimensions ((if viewed stereoscopically via headset, goggles, or glasses). The control panel can be configured to eliminate or minimize any obstruction to the field of view of the surgical environment. For example, portions of the control panel can be transparent or semi-transparent, and the degree of transparency can be adjustable. Alternately or additionally, the surgeon can change the location of the control panel in the modified image, for example, by dragging and dropping the control panel to a desired location.

A control panel can be customized for the surgical system and/or the instrument and/or for a particular procedure or use of the surgical system or instrument. For example, the operating parameters of an endocutter are different from those of a needle driver or an energy-delivering tool, and therefore, the control panel of an endocutter may be different from that of needle driver or an energy-delivering tool. Additionally, the relevant operating parameters of a surgical instrument may change based on the needs of a surgical procedure at any given time. For example, once an endocutter has been positioned in a desired location and clamped on a target tissue, the relevant operating parameters may include articulation angle, knife position, timing of jaw opening, and firing etc. The image of the control panel that is displayed after the endocutter has been clamped onto tissue will include the control for the operating parameters mentioned above.

Figure 1:
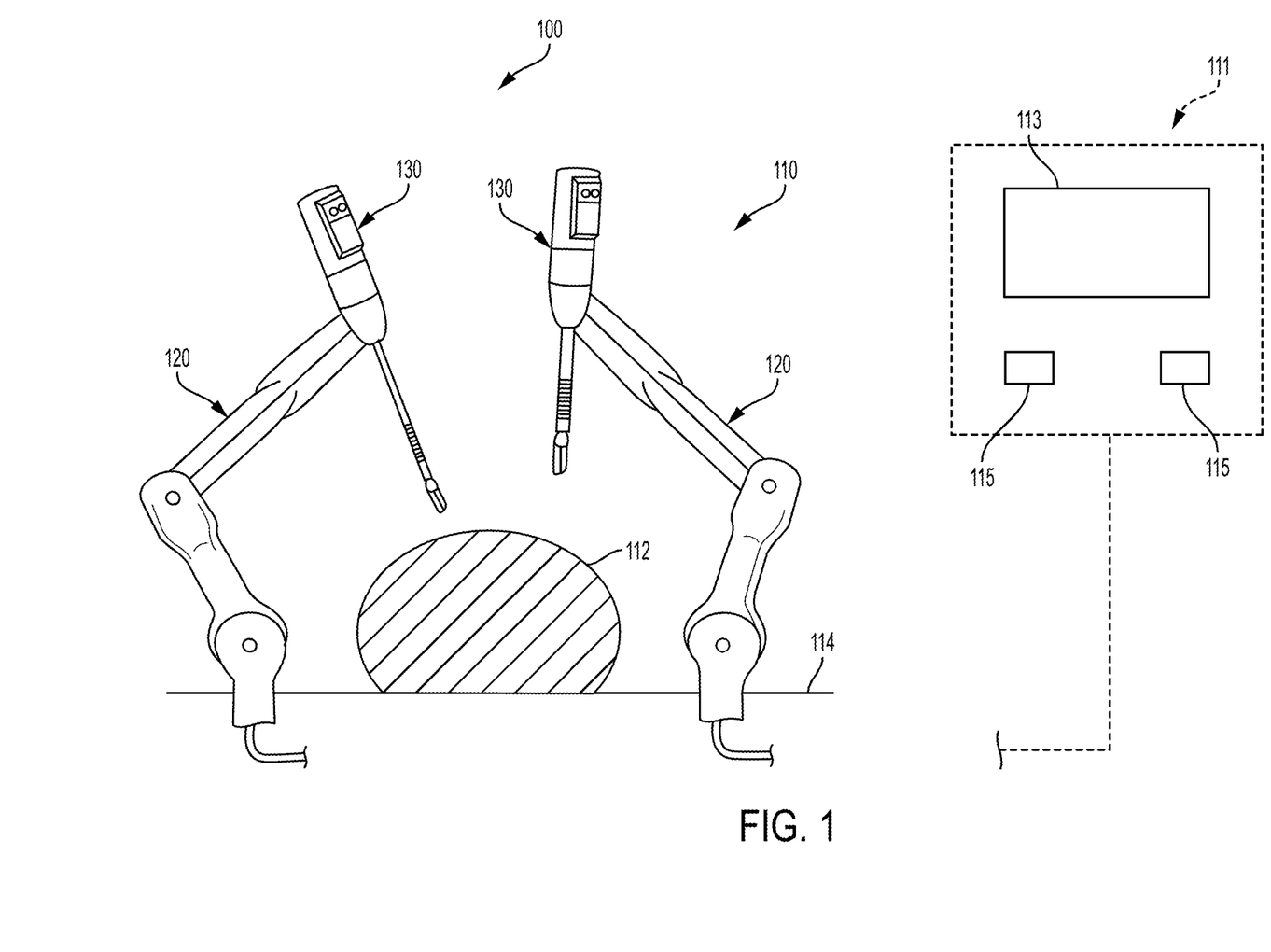
FIG. 1 illustrates a perspective view of an embodiment of a surgical robotic system that includes a patient-side portion and a user-side portion.

FIG. 1 is a perspective view of one embodiment of a surgical robotic system 100 that can be used in telesurgery. The system 100 includes a patient-side portion 110 that is positioned adjacent to a patient 112, and a user-side portion 111 that is located a distance from the patient, either in the same room and/or in a remote location. The patient-side portion 110 generally includes one or more robotic arms 120 and one or more tool assemblies 130 that are configured to releasably couple to a robotic arm 120. The user-side portion 111 generally includes a vision system 113 for viewing the patient 112 and/or surgical environment, and a control system 115 for controlling the movement of the robotic arms 120 and each tool assembly 130 during a surgical procedure.

The control system 115 can have a variety f configurations and it can be located adjacent to the patient, e.g., in the operating room, remote from the patient, e.g., in a separate control room, or it can be distributed at two or more locations. As an example of a dedicated system, a dedicated system control console can be located in the operating room, and a separate console can be located at a remote location. The control system 115 can include components that enable a user to view a surgical environment of a patient 112 being operated on by the patient-side portion 110 and/or to control one or more parts of the patient-side portion 110 (e.g., to perform a surgical procedure at the surgical environment 112). In some embodiments, the control system 115 can also include one or more manually—operated input devices, such as a joystick, exoskeletal glove, a powered and gravity-compensated manipulator, or the like. These input devices can control teleoperated motors which, in turn, control the movement of the surgical system, including the robotic arms 120 and tool assemblies 130.

The patient-side portion can also have a variety of configurations. As depicted in FIG. 1, the patient-side portion 110 can couple to an operating table 114. However, in other embodiments, the patient-side portion 110 can be mounted to a wall, to the ceiling, to the floor, or to other operating room equipment. Further, while the patient-side portion 110 is shown as including two robotic arms 120, more or fewer robotic arms 120 can be included. Furthermore, the patient-side portion 110 can include separate robotic arms 120 mounted in various positions, such as relative to the surgical table 114. Alternatively, the patient-side portion 110 can include a single assembly that includes one or more robotic arms 120 extending therefrom.

Figure 2:
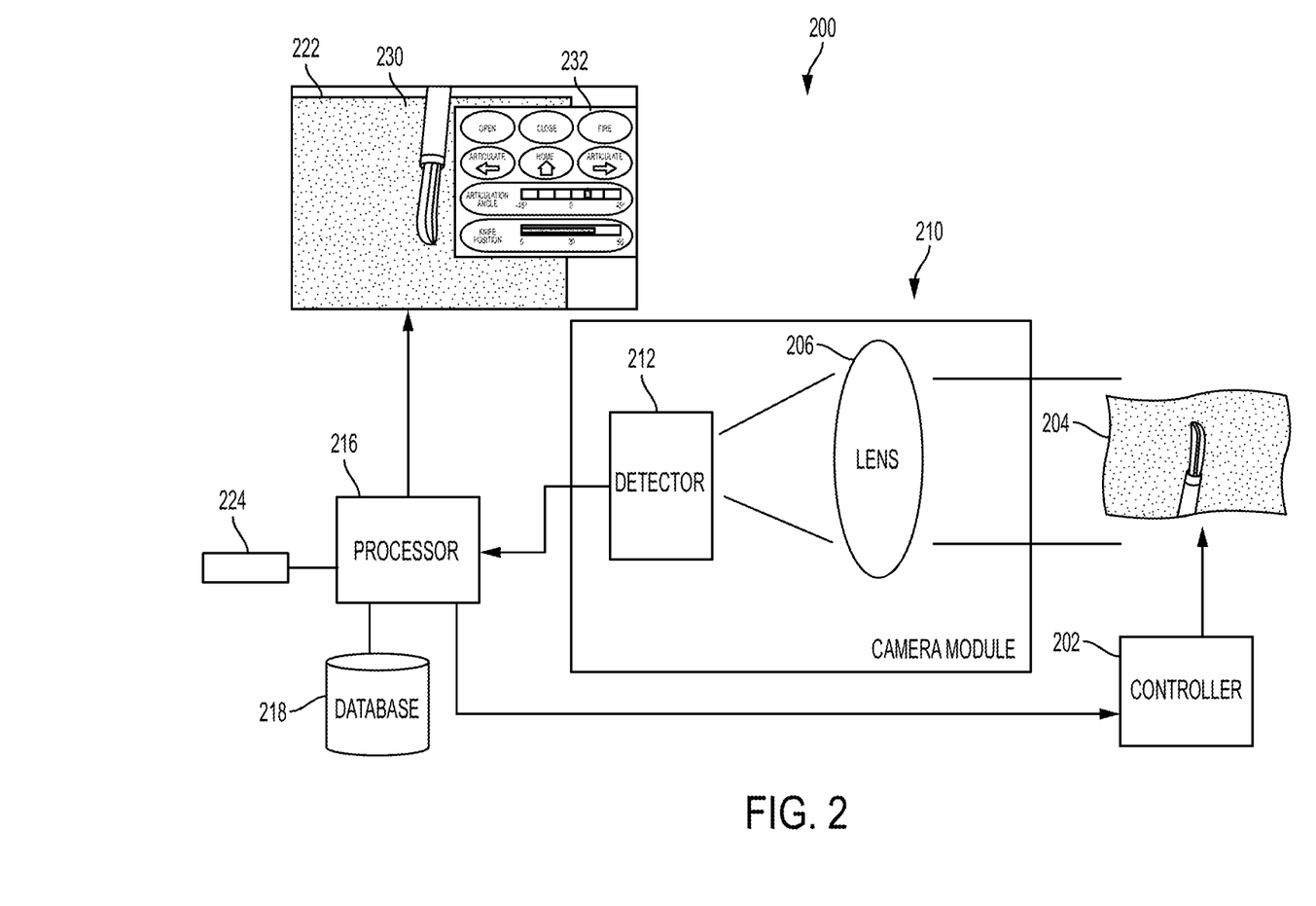
FIG. 2 illustrates a schematic view of a virtual control panel generation system.

FIG. 2 is a schematic view of an example of surgical system 200 configured to generate modified images of a surgical environment (e.g., surgical instrument 204, target tissues, tissues surrounding target tissues, etc.) in real-time. The surgical system 200 includes a surgical instrument 204, a controller 202 to control the operation of the surgical instrument 204, a camera module 210 configured to capture visible-light images of the surgical instrument 204, and relay one or more signals related to the captured image to a processor 216. The processor 216 can also communicate with the controller 202. For example, the processor can receive operating parameters of the surgical instrument 204 from the controller 202, and transmit to the controller 202 control signals that can change the operating parameters. The processor 216 can communicate with a database 218 which can store information related to the surgical instrument 204 (e.g., control panel information). The processor 216 can generate a modified image that includes the visible-light image from the camera 210, and a virtual control panel that allows a user to control the operating parameters of the surgical instrument 204. The modified image can be displayed on a display 222, which can be wall or table mounted or on an accessory worn by the surgeon. The surgical system 200 also includes an input device 224 which can communicate with the processor 216. A user (e.g., surgeon) can interact with the modified image (e.g., change operating parameters in the control panel) using the input device 224. Signals in the surgical system 200 (e.g., between camera module 210 and processor 216, controller 202 and processor 216, input device 224 and processor 216, etc.) can be communicated wirelessly (Bluetooth, WiFi, etc.) or through a data cable (e.g., optical fiber, coaxial cable, etc.).

A light source (not shown) can generate visible light which is reflected by the surgical environment. The reflected light can be visible light (e.g., having a wavelength of about 400 nm to 800 nm) or light of a wavelength that is outside of the visible spectrum (e.g., infrared and ultraviolet light). A portion of the reflected visible-light (e.g., having a wavelength of about 400 nm to 800 nm) is captured by the camera module 210. The camera module 210 comprises a lens 206 configured to focus visible-light onto a detector 212. The quality of the visible-light image can be improved, for example, by placing detector 212 in the focal plane of the lens 206.

Figure 3:
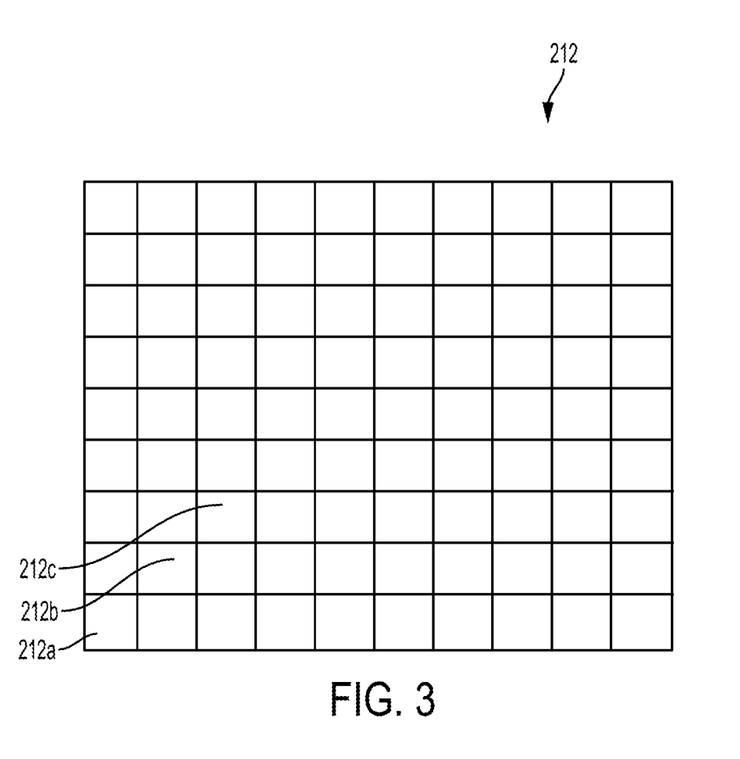
FIG. 3 illustrates a schematic view of a detector in a camera module of the virtual control panel generation system.

The detector 212 is able to detect light reflected by the surgical instrument. As shown in FIG. 3, an exemplary detector 212 comprises an array of photosensitive sites (e.g., 212a-c, etc.), which can absorb electromagnetic radiation impinging on the site, and generate an electrical signal (e.g., voltage signal, current signal, etc.) that is representative of the impinged radiation. For example, the strength of the electrical signal can be proportional to the intensity of the impinged electromagnetic radiation. Photosensitive sites typically have a spectral range which determines the range of frequencies that can be efficiently detected by the site. For example, a silicon (Si) photosensitive site can detect visible to near infrared radiation (spectral range 400-1000 nm), and a germanium (Ge) or indium gallium arsenide (InGaAs) photosensitive site can detect near infrared radiation (spectral range 800-2600 nm). A suitable type of photosensitive site that is appropriate for the spectral range of the electromagnetic radiation that one wants to detect can be selected by a person skilled in the art.

A photosensitive site can be configured to detect a desired wavelength (or a narrow range of wavelength around the desired wavelength) of electromagnetic radiation that lies within its spectral range by using an optical filter. The optical filter, which is placed in the path of the electromagnetic radiation directed towards the photosensitive site, filters out all radiation except for that corresponding to the desired wavelength. For example, a Si photosensitive site (e.g., 212a) with a green color filter will primarily detect green light (approximately 500 nm).

In one example a detector (e.g., detectors 212) detects an image of the surgical environment by combining the images of different regions of the object captured by various photosensitive sites in the detector. When the light reflected by the surgical instrument impinges on the detector 212, a photosensitive site therein (e.g., 212a, 212b, 212c, etc.) detects a part of the reflected light that represents an image of a region of the surgical instrument. The photosensitive site then generates an electrical signal that is representative of the captured image. This electrical signal is converted to a digital signal by an analog-to-digital converter (ADC). The digital signal has discretized values that represent, for example, the intensity of the detected radiation. As will be described below, the digital signal can also include information related to the frequency (color) of the detected radiation. The values of the digital signals from the various photosensitive sites (collectively referred to as an image dataset) are representative of the image of the surgical instrument. There can be a one-to-one relationship between a digital signal value stored in the image dataset, and the photosensitive site that has produced the digital signal value (e.g., the digital signal value can include information that identifies photosensitive site that has generated the digital signal). Therefore, by identifying a digital signal value in the image dataset the photosensitive site that generated the digital value can be identified (or vice-versa). The processor then generates the image of the surgical environment from the image dataset that can be displayed on a display device 222 (e.g., a monitor). Each pixel in the display device can represent one digital signal value in the image dataset. In other words, each pixel in the display device can represent the radiation detected by a unique photosensitive site in the detector 212.

A colored image of a surgical environment can be generated by placing optical filters (or an array of optical filters) in the path of the electromagnetic radiation directed towards a detector. For example, an array of color filters (e.g., Bayer filter, RGBE filter, CYYM filter, CYGM filter, etc.) can be placed before an array of photosensitive sites. As a result, each photosensitive site receives electromagnetic radiation of a particular wavelength (or color). For example, for a Bayer filter, each photosensitive site detects one of red, blue or green color. The processor can use a demosaicing algorithm to process an image dataset obtained using a Bayer filter to generate a "full-color" image (i.e., an image with multiple colors).

If a light optical filter is placed before the first detector 212, it will detect a light image of the surgical environment. As a result, a light image dataset is generated (as described above) and transmitted to the processor 216. The light image dataset can include information related to the intensity and wavelength (color) of the detected light for each photosensitive site.

The controller 202 is configured to control the operation of the surgical instrument 204. For example, if the surgical instrument 204 is an endocutter, the controller can change its operating parameters (e.g., articulation angle, knife position, timing of opening and firing, etc.). The controller 202 can also control the energy delivered by the surgical instrument 204 to a target tissue. For example, the controller 202 may drive an ultrasonic transducer in the surgical instrument and/or generate radio frequency energy which the surgical instrument can deliver to a tissue through an energy-delivering end effector. The controller 202 is configured to receive control signals from the processor 216 and such control signals can change the operating parameters of the surgical instrument 204. The controller 202 can transmit a signal to the processor 216 that includes information related to the operating parameters and identity of the surgical instrument 204. The signal may be transmitted when the controller 202 receives a request signal from the processor 216 requesting information related to the surgical instrument 204. The controller 202 can include a memory device that has a log file which keeps track of the operating parameters of the surgical instrument 202. The log file (or a part thereof) can be transmitted to the processor 216. In some embodiments, the processor 216 and the controller 202 may not communicate directly. For example, their communication may be routed through one or more devices (e.g., processors, routers etc.).

The processor 216 can identify the surgical instrument 204 and its operating parameters, for example, based on the signal from the controller 202. Processor 216 can access information associated with the surgical instrument 204 that may be stored in the database 218 or that may be communicated to the processor from the surgical instrument itself. For example, the processor may search the database 218 for a template of a virtual control panel related to surgical instrument 204, or it can receive such a template from the surgical instrument. The database may also contain a control panel template that has been customized by the user based on their specific requirements. The choice of the template may also be based on the operating parameters of the surgical instrument 204. The processor 216 can modify the light image of the surgical environment obtained from the camera module 210 by superimposing the control panel 232 onto the image. The modified image can be displayed on the display 222.

As shown in FIG. 2, the modified image includes the image of the surgical environment 230 and the control panel 232. As explained above, the control panel can be located at a fixed location on the display 222 (e.g., top left, top right, bottom left, bottom right, etc.) or the location of the control panel can change, such as based on user commands. Moreover, a user can interact with the control panel 232 through the input device 224. For example, if the input device 224 is a user interface device, processor 216 can generate a pointer in the modified image that can track the motion of the user interface device. The user can use the user interface device to scroll, drag, actuate (e.g., click, double click, etc.) on various control elements in the control panel. If the user is operating in a 3D environment (i.e., via a stereoscopic camera system) the input device 224 may appear to the user as a 3D pointer that moves within the 3D space surrounding the device and/or control panel. Based on this input, the processor 216 can generate a control signal to change one or more operating parameters, and such a control signal is transmitted to the controller 202.

Figure 4:
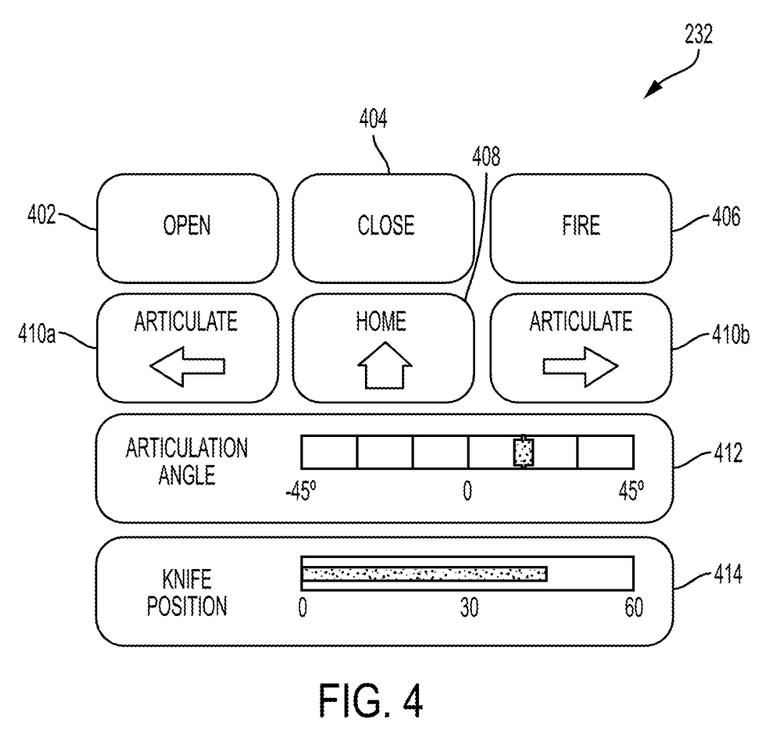
FIG. 4 illustrates an example of a virtual control panel of the system described herein.

FIG. 4 illustrates an example of the control panel 232 when the surgical instrument 204 is an endocutter. As shown, the control panel 232 comprises various control elements or buttons (402-414). The user may open or close the jaws of the endocutter by actuating virtual buttons 402, 404, respectively. The user may change the articulation angle to the left or right by actuating virtual buttons 410a and 410b, respectively, and button 408 can be actuated to return the tool to its home position. Window 412 within control panel 232 indicates the degree of articulation associated with the surgical instrument. In another functionality, the user can control the knife action by actuating fire button 406 to cause the knife to fire. Part of the virtual control panel also includes a knife position tab 414. In one embodiment the control elements in windows 412, 414 can be used to change the articulation angle and the knife positon, respectively, although it is understood that windows 412, 414 can be configured only to display information and not to enable control of the instrument.

As noted above, a user can vary the degree of transparency of the control panel 232. For example, if the transparency of the control panel is lowered, the visibility of the surgical environment behind the control panel decreases and vice versa. The user may want to adjust the transparency of the control panel, for example, when the control panel is overlaid on an area of the surgical environment that needs to be monitored (e.g., target tissue). Alternately, the user may move the control panel in the modified image (e.g., by dragging and dropping using the input device 224).

Figure 5:
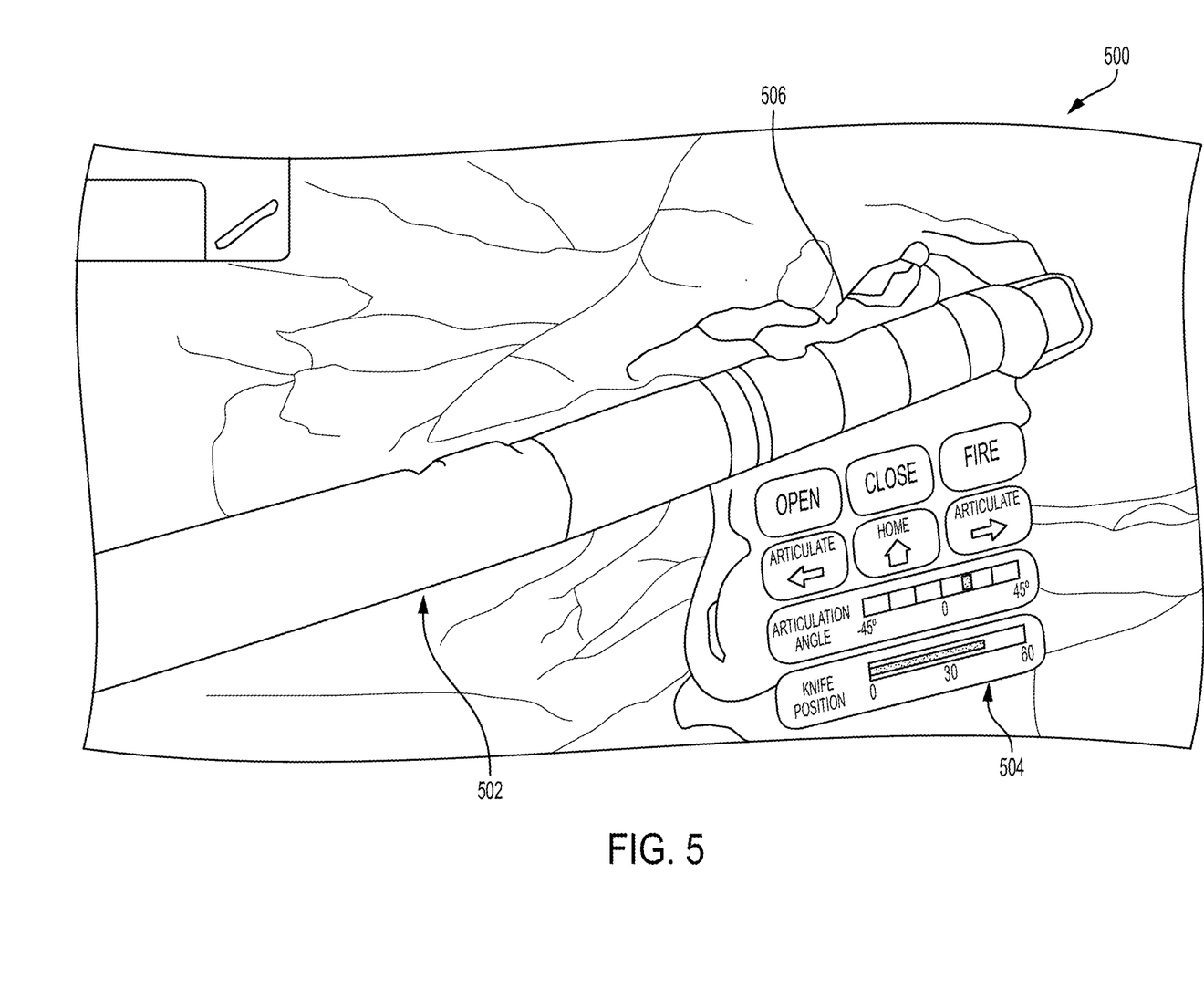
FIG. 5 illustrates an example of a modified image of a surgical instrument that includes the virtual control panel.

As described above, in some embodiments of the surgical system 200, the control panel 232 can follow the motion of the surgical instrument 204 in the modified image. The processor 216 can be configured to identify the image of the surgical instrument 204 from the image of the surgical environment (obtained from the camera module 210), and superimpose the control panel 232 at a fixed position relative to the image of the image of the surgical instrument. As the surgical instrument 204 moves, the control panel 232 follows its motion. FIG. 5 illustrates an example of a modified image 500 of an endocutter 502 performing a surgical procedure on a target tissue 506. The control panel 504 is located near the distal end of the endocutter so that it is most easily viewed by a surgeon. The control panel 506 can be configured to appear after the endocutter is locked to the location, for example, by the release of a clutch pedal by the user. In another embodiment, the control panel 232 can be located on or near the shaft of the endocutter.

The processor can identify data related to the image of the surgical instrument 204 (e.g., endocutter) from the reflected light image dataset generated by the camera module 210. In one embodiment, the data is identified based on a predetermined relative position between the first detector 212 and the surgical instrument 204. In this embodiment, the camera module 210 is attached to the surgical instrument 204 such that the relative position of the surgical instrument with respect to the camera module 210 remains fixed. This can be done, for example, by having a mounting feature on the surgical instrument to which the camera module 210 can be removably attached. Devices (detector 212, lens 206, etc.) inside the camera module 210 can be positioned in a predetermined configuration. Alternately, the devices can be attached to piezoelectric actuators that allow them to move relative to one another. This can allow the detector to detect a sharp image of the surgical instrument. For example, it can be desirable to place the detector 212 in the focal plane of the lens 206. Mechanical movements and thermal expansion of the camera module 210 and the devices therein can move the detectors out of the focal plane of the lens. The detectors can be adjusted back into the focal plane by the piezoelectric actuators that can be controlled by the processor 216, or by an input from a user. The surgical instrument 204 and the camera module 210 (and the devices inside the camera module) can be adjusted to a desired predetermined position prior to the insertion of camera module 210 and surgical instrument 204 in the surgical environment. The photosensitive sites in detectors 212 that capture the image of the surgical instrument 204 can be identified based on the predetermined orientation of the detector 212 and the surgical instrument 204. Information related to the location of the aforementioned photosensitive sites can be stored in the database 218. The processor 216 can identify surgical instrument image data in the reflected light image dataset. This can be done, for example, by arranging the image data, captured by the photosensitive sites, in a predetermined pattern in the light image. For example, the image data captured by the photosensitive site 212a can be placed at a predetermined location in the visible-light dataset. Information about this relationship can be stored in an index data file in the database 218. Based on the index data file, the processor 218 can identify the image data (from the reflected image dataset) corresponding to the image detected by the photosensitive site 212a. Alternately, the image data can include information that identifies the photosensitive site that generated it.

Figure 6:
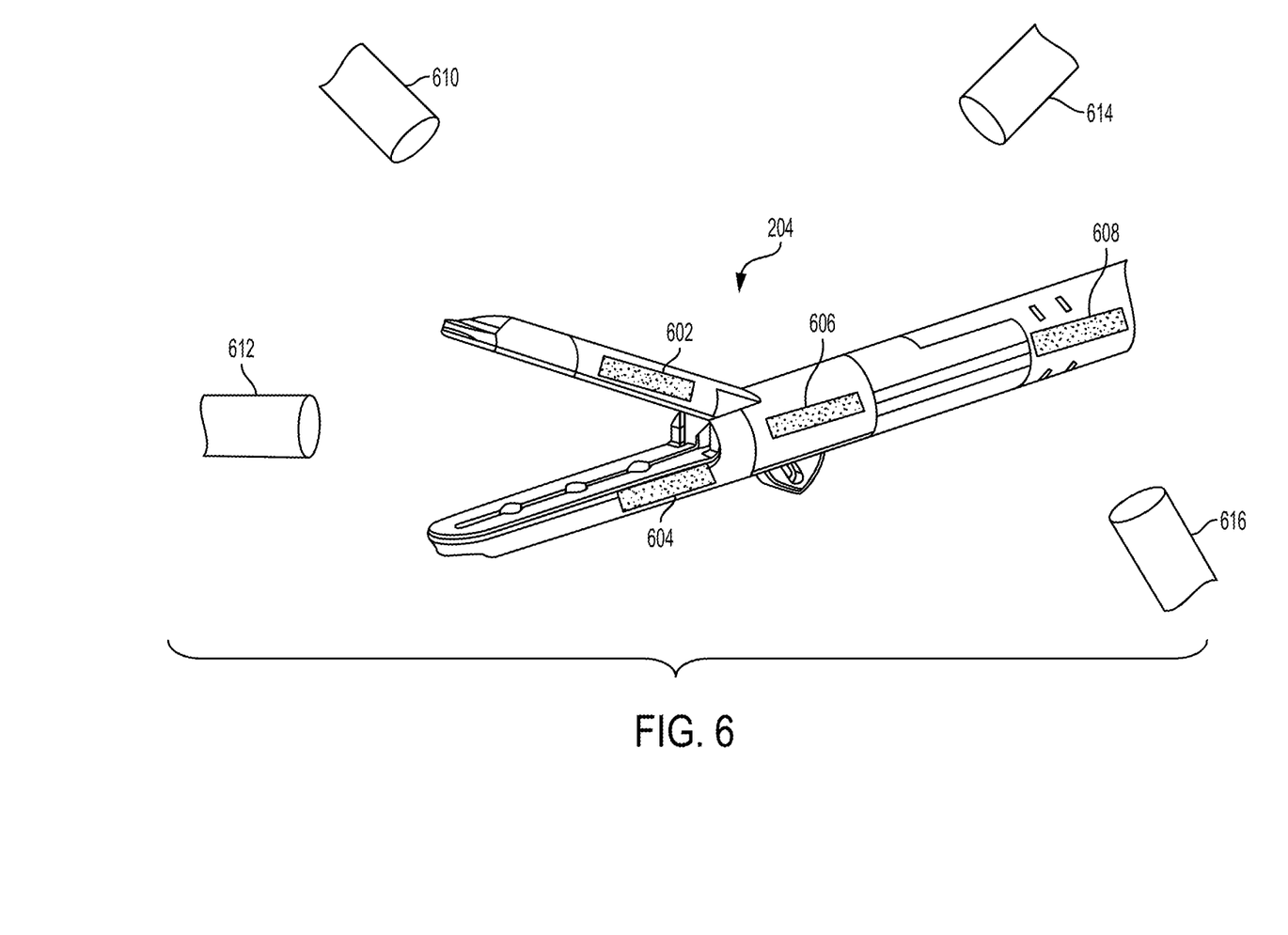
FIG. 6 illustrates a surgical instrument positioned in a field having multiple markers.

In another embodiment, the surgical instrument is identified in the light image based on one or more markers on the surgical instrument 204, and multiple cameras 610, 612, 614, 616 are used to image the surgical environment. As shown in FIG. 6, the surgical instrument 204 includes a number of markers 602, 604, 606, 608 located on its surface. In one embodiment the markers are regions on the surgical instrument 204 that reflect electromagnetic radiation of a given frequency. For example, the markers can be configured to reflect light of a certain color. The color of the markers can be selected such that the color is not naturally present in the surgical environment (e.g., green, blue, etc.). The processor 216 thus identifies photosensitive sites that detect the image of the markers based on marker color. As described above, the reflected light image dataset can include, for each photosensitive site, information related to the color of the detected light. The processor can search in the reflected light image dataset for data representative of the color of the marker. The processor 216 identifies the markers 602, 604, 606, 608 (and therefore the relative positions of the markers) in the reflected light image and compares this information with data from a database of surgical instruments stored in the database 218. The database includes information related to marker color and marker position for various surgical instruments. Additionally, for a given surgical instrument, the database may include information related to the relative position of the makers in an image of the surgical instruments from multiple viewpoints. For example, the relative positions of the markers 602, 604, 606, 608 in the image of the surgical instrument 204 in the embodiment of FIG. 6 will depend on the relative position of the camera (e.g., 610, 612, 614, 616) that captures the image.

The processor can use an image recognition algorithm to identify the data in the visible-light dataset that represents the image of the surgical instrument. In one example the image recognition algorithm receives input information related to the position of the markers in the captured image, and information related to various surgical instruments stored in the database 218. The processor compares the relative positions of markers in the captured image with the orientation information of markers of the devices in the database 218 by using various pattern recognition techniques. Based on this comparison, the processor can identify data representative of image of the surgical instrument in the visible-image dataset. Additionally or alternatively, the processor can use a pattern recognition algorithm and/or device database to work with devices that are not readily known to or controlled by the robotic surgical system (i.e., a hand-operated stapler, retractors, etc.) It is to be understood that markers may comprise a specific geometric shape and/or color, either as something that is applied to the device (e.g., green dots) or the color can be inherent of typical devices (e.g., silver straight jaws and blackened shaft).

After the processor 216 identifies the image of the surgical instrument 204, it can provide the user of the surgical system 200 with an option to choose the location of the control panel 232. The user may drag the control panel 232 to a desired orientation relative to the image of the surgical instrument in the modified image (e.g., at the proximal or distal ends of the surgical instrument, shaft of the surgical instrument, etc.) and lock the position of the control panel 232. As the image of the surgical instrument 204 moves in real-time, the orientation of the control panel 232 is accordingly adjusted to maintain the locked relative orientation.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to a user and a keyboard and a pointing device, e.g., a mouse, a trackball, etc., by which a user may provide input to the computer. Other kinds of devices can be used to provide for interaction with a user as well. For example, feedback provided to a user can be any form of sensory feedback, such as for example visual feedback, auditory feedback, or tactile feedback; and input from a user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 7:
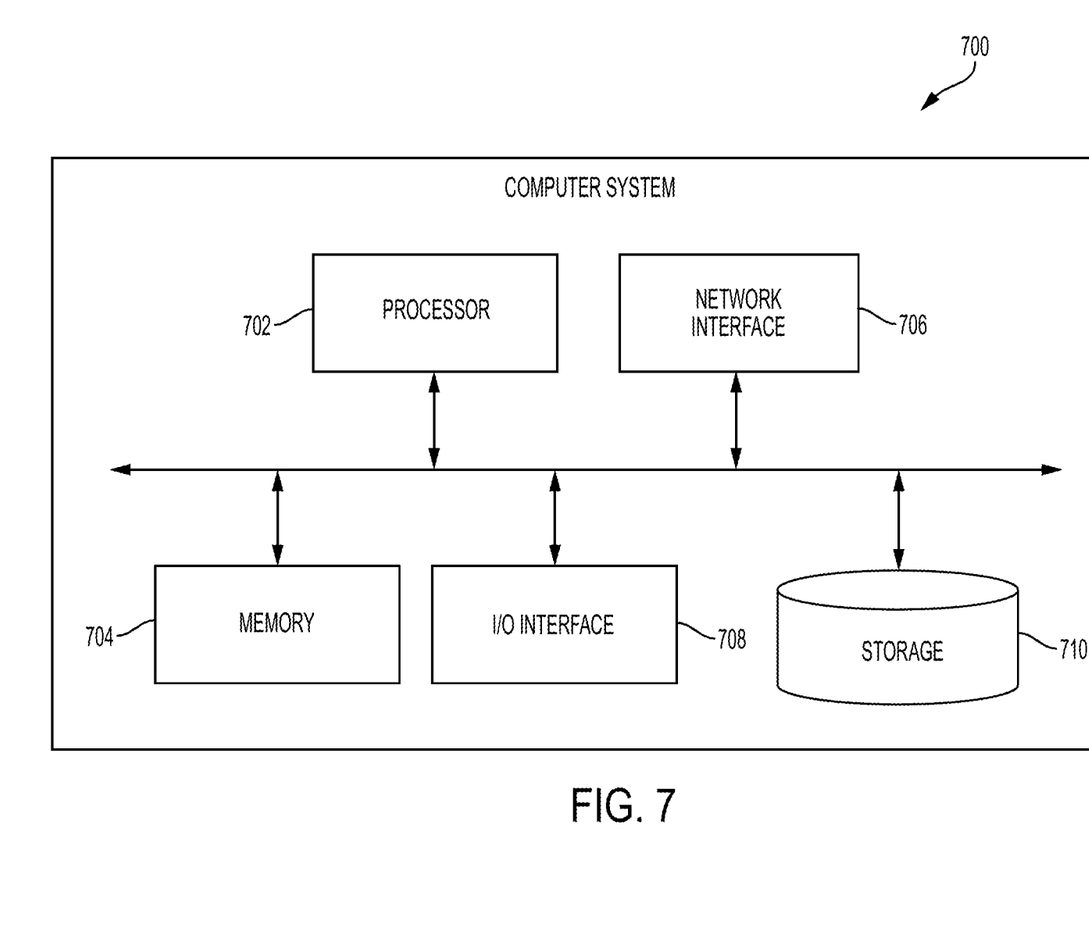
FIG. 7 is a schematic illustration of a computer system configured to generate a plurality of command signals for use with the control system described herein.

FIG. 7 illustrates an exemplary embodiment of a computer system 700. As shown, the computer system 700 includes one or more processors 702 which can control the operation of the computer system 700. "Processors" are also referred to herein as "controllers." The processor(s) 702 can include any type of microprocessor or central processing unit (CPU), including programmable general-purpose or special-purpose microprocessors and/or any one of a variety of proprietary or commercially available single or multi-processor systems. The computer system 700 can also include one or more memories 704, which can provide temporary storage for code to be executed by the processor(s) 702 or for data acquired from one or more users, storage devices, and/or databases. The memory 704 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 700 can be coupled to a bus system 712. The illustrated bus system 712 is an abstraction that represents any one or more separate physical busses, communication lines/interfaces, and/or multi-drop or point-to-point connections, connected by appropriate bridges, adapters, and/or controllers. The computer system 700 can also include one or more network interface(s) 706, one or more input/output (IO) interface(s) 708, and one or more storage device(s) 710.

The network interface(s) 706 can enable the computer system 700 to communicate with remote devices, e.g., other computer systems, over a network, and can be, for non-limiting example, remote desktop connection interfaces, Ethernet adapters, and/or other local area network (LAN) adapters. The IO interface(s) 708 can include one or more interface components to connect the computer system 700 with other electronic equipment. For non-limiting example, the IO interface(s) 708 can include high speed data ports, such as universal serial bus (USB) ports, 1394 ports, Wi-Fi, Bluetooth, etc. Additionally, the computer system 700 can be accessible to a human user, and thus the IO interface(s) 708 can include displays, speakers, keyboards, pointing devices, and/or various other video, audio, or alphanumeric interfaces. The storage device(s) 710 can include any conventional medium for storing data in a non-volatile and/or non-transient manner. The storage device(s) 710 can thus hold data and/or instructions in a persistent state, i.e., the value(s) are retained despite interruption of power to the computer system 700. The storage device(s) 710 can include one or more hard disk drives, flash drives, USB drives, optical drives, various media cards, diskettes, compact discs, and/or any combination thereof and can be directly connected to the computer system 700 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 7 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 700 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 700 can also include a web server for generating and/or delivering the web pages to client computer systems.

In an exemplary embodiment, the computer system 700 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system comprising:
a detector, comprising an imaging device configured to detect light reflected by a surgical instrument and a target tissue and generate a first signal comprising a first dataset representative of an image of the surgical instrument and the target tissue;
a processor configured to:
receive the first signal,
receive a second signal indicative of coupling between the surgical instrument and the target tissue,
generate, after the receipt of the second signal, a modified image of the surgical instrument and the target tissue that includes a control panel, wherein the control panel comprises one or more control elements representative of one or more operating parameters of the surgical instrument,
receive an input to the control panel from a user via an input device configured to be held by the user, the input being effective to change one of the operating parameters,
generate a command signal based on the input to the control panel to change one of the operating parameters.

2. The system of claim 1, wherein the modified image is displayed on a display device.

3. The system of claim 1, wherein the processor identifies data from the first dataset data that is representative of the surgical instrument based on a position of the detector with respect to the surgical instrument.

4. The system of claim 1, wherein at least one of position and shape of the control panel in the modified image is adjusted based on the orientation of the surgical instrument.

5. The system of claim 1, wherein the position of the control panel with respect to the surgical instrument remains fixed.

6. The system of claim 1, further comprising an input device to receive the input from the user, wherein the input device is a user interface device.

7. The system of claim 1, wherein the processor generates a pointer that moves relative to the modified image based on the input by the user.

8. The system of claim 7, wherein the command signal is generated when the user actuates one of the one or more control elements using a user interface device.

9. The system of claim 1, wherein the surgical instrument is one with functionality including at least one of tissue cutting, tissue stapling, and delivery of energy to tissue.

10. The system of claim 1, wherein the processor receives a second signal representative of information related to the surgical instrument.

11. The system of claim 10, wherein the control panel is generated based on the second signal and data related to the surgical instrument that is stored in a database.

12. The system of claim 1, further comprising:
a robotic arm; and
a tool assembly removably coupled to the robotic arm and comprising a shaft extending distally from a housing and the surgical instrument is coupled to a distal end of the shaft.

13. The system of claim 2, wherein the display device is at least one of a wall mounted display, a table mounted display, and a display on an accessory worn by a surgeon.

14. The system of claim 6, wherein the processor generates a pointer that moves relative to the modified image, based on the input by the user.

* * * * *